United States Patent [19]

Burd

[11] 4,184,489
[45] Jan. 22, 1980

[54] INFUSION TUBE ACCESS SITE
[75] Inventor: Samuel Burd, Oakland, Calif.
[73] Assignee: Cordis Dow Corp., Miami, Fla.
[21] Appl. No.: 856,383
[22] Filed: Dec. 1, 1977

Related U.S. Application Data

[63] Continuation-in-part of Ser. No. 729,940, Oct. 6, 1976, abandoned.

[51] Int. Cl.² .................. A61M 5/00; A61M 1/03; F16L 11/12
[52] U.S. Cl. .................. 128/214 R; 138/103; 138/152; 138/178
[58] Field of Search .............. 138/103, 178, 137, 152; 128/214 R, 214 C, 214.2, 214.4

[56] References Cited

U.S. PATENT DOCUMENTS

| | | | |
|---|---|---|---|
| 3,447,570 | 6/1969 | Collins | 138/103 |
| 3,486,531 | 12/1969 | Nalodka | 138/103 |
| 3,814,137 | 6/1974 | Martinez | 138/103 |
| 3,850,202 | 11/1974 | Morgan | 138/103 |
| 3,898,988 | 8/1975 | Morgan | 138/103 X |
| 3,990,445 | 11/1976 | Lundquist | 138/103 X |
| 4,076,023 | 2/1978 | Martinez | 138/103 X |

Primary Examiner—Richard E. Aegerter
Assistant Examiner—James E. Bryant, III
Attorney, Agent, or Firm—Neal A. Waldrop

[57] ABSTRACT

An extra corporeal blood tube injection site comprising a smooth blood conduit or tube, an elongated elastomeric sleeve surrounding a section of the tube, and a C-shaped needle-impenetrable member extending along and partially surrounding the sleeve which generates forces within the portion of the sleeve that is not covered by the C-shaped member sufficient to prevent air leakage into, or blood leakage from, the tube during needle penetration or after withdrawal of a needle.

4 Claims, 9 Drawing Figures

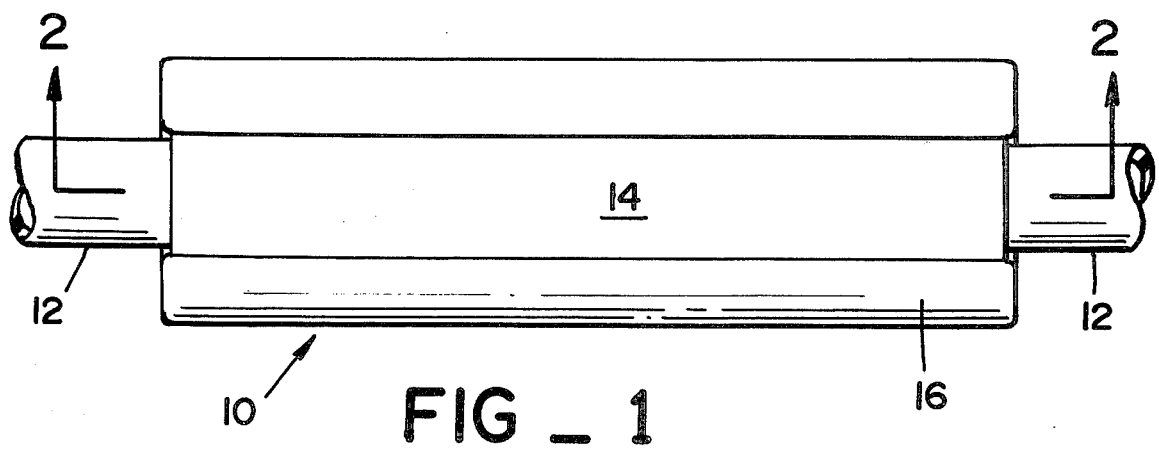
FIG _ 1
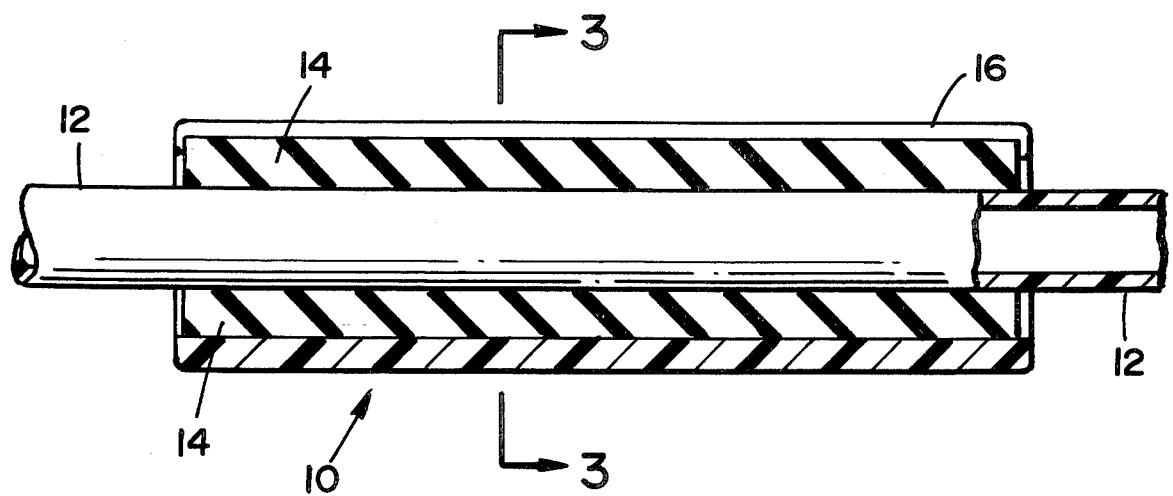
FIG _ 2
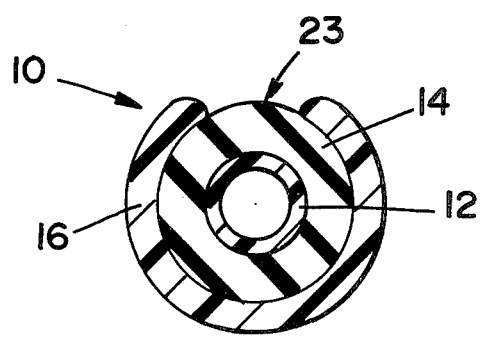
FIG _ 3

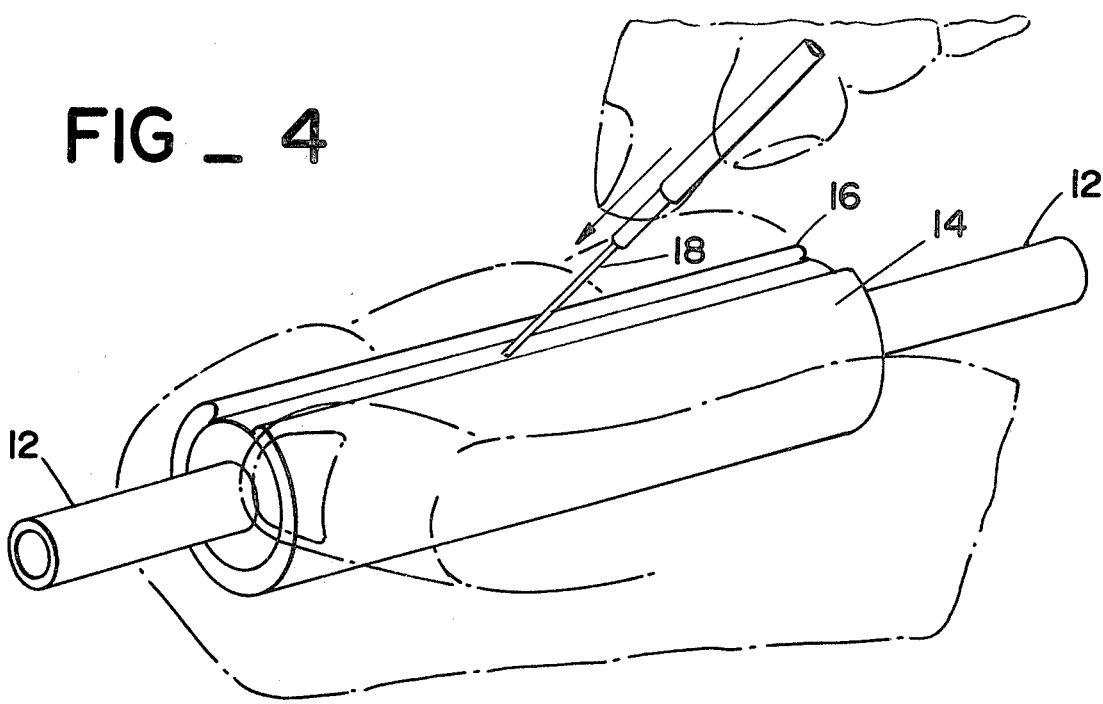
FIG_4
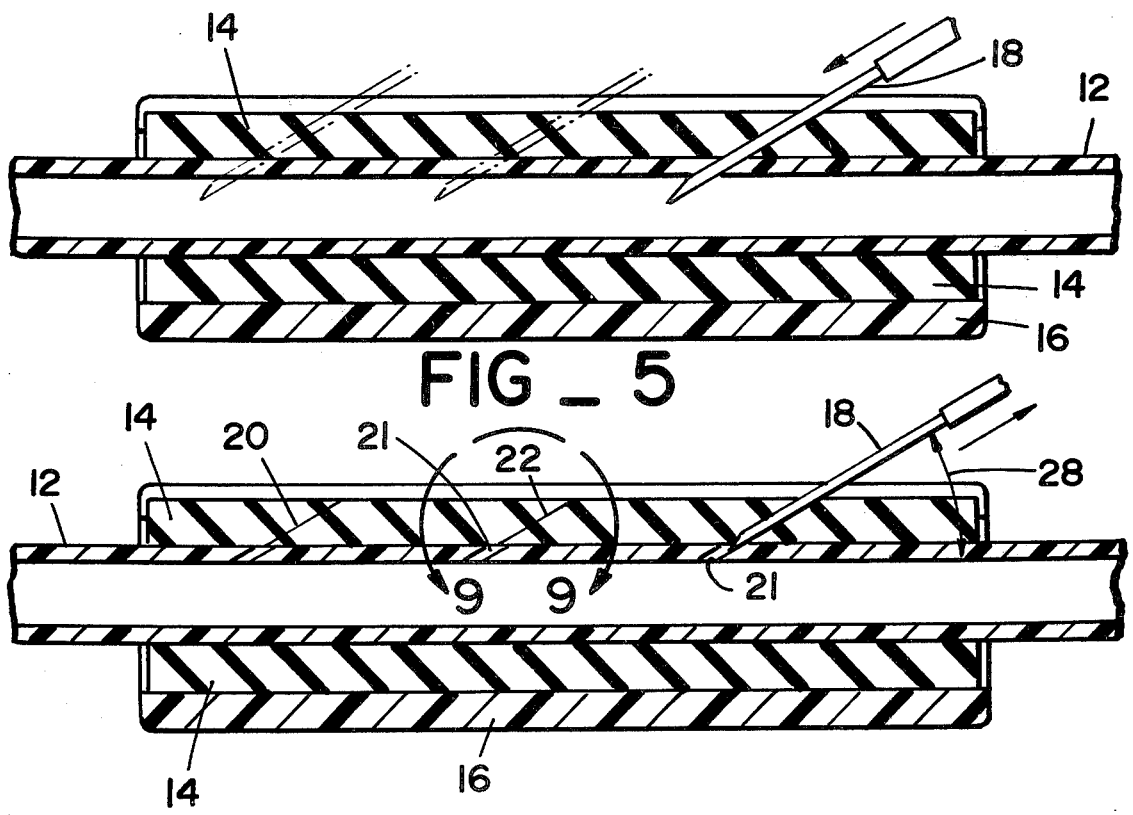
FIG_5
FIG_6

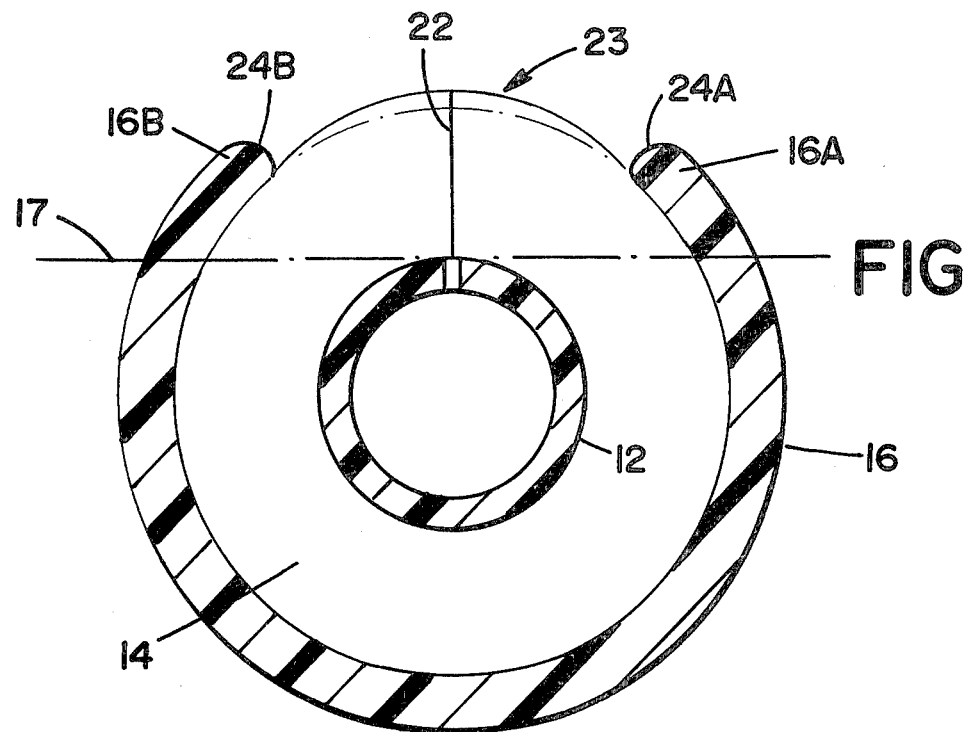
FIG_7
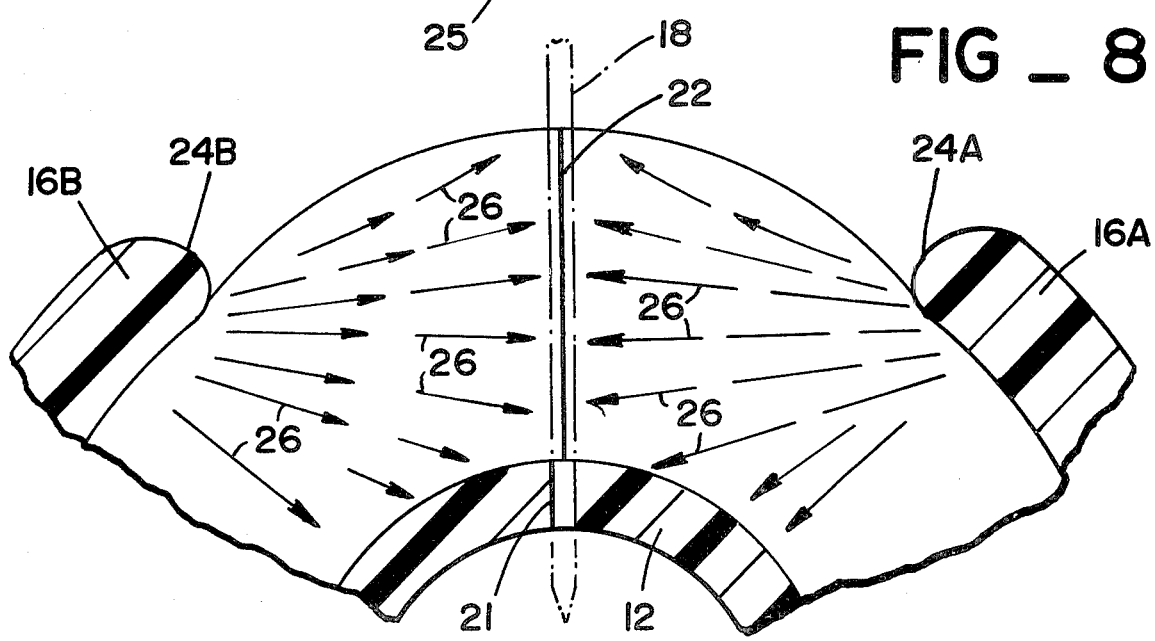
FIG_8
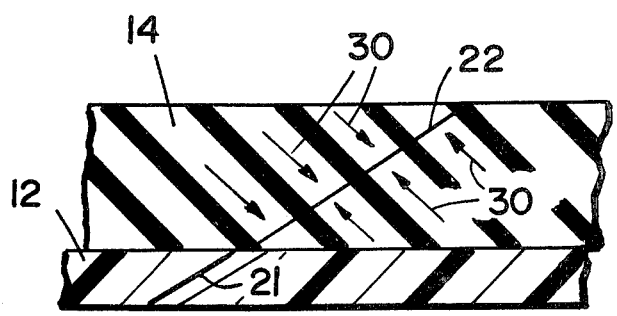
FIG_9

INFUSION TUBE ACCESS SITE

BACKGROUND OF THE INVENTION

This application is a continuation-in-part of copending application Ser. No. 729,940 filed Oct. 6, 1976, now abandoned.

This invention relates to an improved construction of the site on a tube external of a patient to enable leak-free withdrawal of fluid samples from, or the injection of medicants into, a fluid flowing in the tube. The invention is particularly useful in blood tube sets used for the passage of blood between the patient and an artificial kidney or a blood oxygenator.

Commercial blood-passage tubing sets have typically provided one or more injection sites at which blood samples may be taken from, or chemicals injected into, the blood by hypodermic needle piercing the tube wall. Smooth, nontoxic tubing must be used for the blood passage for patient safety; such tubing has relatively thin walls, little elasticity and is typically non-sealing after being pierced. In order to prevent leakage into or from blood tubing pierced with a hypodermic needle, elastomeric materials having some ability to self-seal have been used in the past. The elastomeric material is so arranged with the blood tube that the needle puncture is made through the self-sealing elastomeric material before piercing the tube. However, the self-sealing characteristic of the best commercially available material, natural rubber latex, is insufficient at times to prevent leakage into the blood tube during needle penetration or to effect sealing after needle withdrawal, under some of the conditions of use which are periodically encountered. For example, the difficulty of self-sealing increases as the needle size increases, as the time of needle penetration increases, and as the number of repeat injections is made at a particular injection site. Moreover, the best known self-sealing material, natural rubber latex, is known to have toxicity and blood clotting characteristics that are less desirable than other elastomeric materials such as silicone rubber, polyurethane elastomers, etc.

To overcome the leakage problem while concurrently avoiding toxicity or blood clot formation many injection site constructions have heretofore been proposed. Commercial tube sets have used a latex sleeve surrounding a section of the blood tubing and prevented leaks by using plastic or metal ties to apply sealing pressure. Other site constructions have relied on the inherent self-sealing of the sleeve to prevent leakage such as shown in U.S. Pat. No. 3,447,570. To further insure against leakage, another construction surrounds a latex sleeve with a second thin, latex sleeve stretched over the first sleeve and extending beyond the ends of the first sleeve to also seal against the blood tube. This latter construction is shown in U.S. Pat. No. 3,814,137. While this construction has experienced some commercial acceptance, it is nevertheless subject to leakage under severe use conditions. It is further objectionable because of the hazard of piercing the holding hand of the person as the elastomeric sleeves and the tube are pierced.

A blood access site construction which purports to eliminate hazard to the needle administrator and leakage is shown in U.S. Pat. No. 3,898,988. This construction employs a plastic tube section which is placed in the blood flow conduit. This plastic tube is a T-shaped hard plastic body having a bore extending for the length of the vertically disposed body portion and a diameter sufficient to receive the ends of blood tubes which are adhesively secured in the bore. In the longitudinal central area of the T-shaped section the bore diameter in the plastic body equals the inner diameter of the blood tubes and the blood flows through that plastic bore between the inner ends of each blood tube. Injection is made through an axially small cylindrical opening in the top surface of the T-shaped section which overlies the bore in the tube body through which the blood is flowing; the small cylindrical opening is filled with an insert of a non-thrombogenic elastomer such as a polyurethane or silicone rubber which is radially compressed into place in the opening. This construction has the serious defects that the lower end of the elastomer is in contact with the blood flowing through the plastic body and the entire cylindrical elastomer insert is subject to dislodgement as the hypodermic needle is withdrawn; dislodgement of the radially compressed elastomeric insert creates a channel for leakage having the same diameter as the blood tube diameter which is highly dangerous and obviously unacceptable. The construction of U.S. Pat. No. 3,898,988 and the related construction of U.S. Pat. No. 3,850,202 provide a limited axial length of availability for plural penetrations into the flowing blood stream and neither construction involves the problem of post-penetration sealing of normally non-self-sealing blood tubing; each of these constructions directly penetrates the blood interface at the inner surface of the elastomeric material which is subjected to radial pressure.

The above described constructions represent the closest prior art known to applicant which also includes the references cited during their prosecution, viz. U.S. Pat. Nos. 2,129,983; 2,498,831; 2,832,338; 3,030,955; 3,112,748; 3,447,570; 3,463,691; 3,853,127; 2,053,112; 2,907,351; 3,566,868 and others cited during the prosecution of parent application Ser. No. 729,940, viz., 2,653,606, 3,486,531, 3,566,868 and 3,990,445. None of the constructions known to applicant completely solve the problems of leakage into, or from, a continuous blood tube while simultaneously eliminating the hazard of accidental piercing of the hand of the needle administrator.

The present invention solves both of these problems and provides an inexpensive, substantially leak-free blood tube access device.

BRIEF SUMMARY OF THE INVENTION

This invention provides an inexpensive infusion tube access site comprising a smooth nontoxic tube having an elongated elastomeric sleeve surrounding a section of the tube that is improved and distinguished from prior constructions by an axially slotted tubular needle-impenetrable member substantially co-extensive in length with the sleeve and enveloping more than one-half of the periphery of the elastomeric sleeve; the wall portions which extend above the diameter of the tubular needle-impenetrable member define the slot which extends from one end to the other of the tube. The width of the slot is relatively narrow and normally varies from about 10° of arc to about 35° of arc and preferably is between about 10° and 25° of arc. The wall thickness of the slotted tubular member is selected, in conjunction with the internal resistance of the selected plastic material to be deformed from a circular cross-section to exert a squeeze force on the encompassed elastomeric sleeve sufficient to effectively seal against air leakage into, or blood leakage from, the blood tube during needle insertion or after the needle is withdrawn. The site construction of this invention protects against inadvertent injury to the hand holding the needle-impenetrable member during needle insertion, and provides a large access area for making plural insertions at various angles of needle placement for injecting medications and collecting blood samples. The site construction of this invention also provides improved resistance to leaks under much more severe conditions of use than those normally encountered in the ordinary use of blood sets for blood passing between a patient and an artificial kidney or a blood oxygenator; it is also useful in transfusing blood or other fluids, such as saline solutions, etc.

DESCRIPTION OF THE DRAWINGS AND DETAILED DESCRIPTION OF THE PREFERRED EMBODIMENT

FIG. 1 is a top view of a preferred embodiment of the invention.

FIG. 2 is a view taken on the line 2—2 of FIG. 1.

FIG. 3 is a view taken on the line 3—3 of FIG. 2.

FIG. 4 is a perspective view, partly broken away, showing the preferred embodiment during needle insertion.

FIG. 5 is a view of the embodiment of FIG. 4, in section, showing one needle piercing the elastomeric sleeve and blood tube wall and two additional piercing locations of a needle in dotted lines.

FIG. 6 is a view illustrating a site of this invention which shows two withdrawn needle locations and a third needle partially withdrawn.

FIG. 7 is an enlarged end view of the embodiment of FIG. 1.

FIG. 8 is an enlargement of the needle penetrating portion of FIG. 7 showing the force distribution within the elastomeric sleeve as a needle is withdrawn.

FIG. 9 is an enlargement of the portion of FIG. 6 surrounded by the line 9—9 showing the force distribution within the elastomeric sleeve on a needle inserted at an angle less than 90° to the axis of the blood tube.

Referring to the drawings, the improved access site construction of this invention is shown in FIG. 1 and generally designated 10. Site 10 consists of blood or infusion tube 12 which in normal use is a part of the blood tubing in a tube set which connects patient's artery or vein to an artificial kidney or blood oxygenator, or an organ perfusion device. Tube 12 may be made of any of a number of commercially available nontoxic plastics, for example, polyvinyl plastisols, polyurethane or silicone rubber and preferably is made of plasticized polyvinyl chloride.

An elastomeric sleeve 14 surrounds a section of tube 12 at one or more locations along its length, for example, in sections about 1 to 2½ inches long. The elastomeric properties of sleeve 14 are important to the accomplishment of the objective of elimination of leaks of the types above mentioned. The elastomer should be relatively soft and yet have sufficient elasticity and internal strength to permit needle insertion without shredding or disintegrating as the needle is inserted or withdrawn; it should exhibit maximized memory or ability to resume its original position after being stretched or deformed and maximum resistance to fatigue or change of resilience with reuse or passage of time. Importantly, the elastomer should be capable of transmitting forces, particularly compressive forces, from the point of application to adjacent areas within the body of the elastomer. These general considerations can be employed in selecting the best elastomer for particular use conditions which may vary substantially as to pressure of fluid flowing in tube 12, or the diameter of the needle used, or the time of retention of the needle during the blood sampling or during the addition of medicants to the blood tube from those conditions which are normally encountered in the use of access sites on blood sets employed in dialyzing a patient with an artificial kidney. There are a number of types of elastomeric materials which are available from which sleeve 14 may be fabricated that will possess the appropriate degree of resiliency for a specific set of use conditions, for example, polyurethane elastomers, silicone elastomers, synthetic latex and natural rubber latex. For use in dialysis of humans employing an artificial kidney, particularly the type of artificial kidney containing hollow fibers as the dialyzing element such as the C-DAK artificial kidney available from Cordis Dow Corp., the preferred elastomer is natural rubber latex.

The third, and key, element in the preferred access site construction of this invention is the axially slotted tubular needle-impenetrable element 16, which surrounds a portion of the periphery of sleeve 14, greater than one-half of that periphery, and preferably about 65% to about 90% of it. Element 16 has as its first function the prevention of inadvertent penetration by needle 18 completely through sleeve 14 and tube 12 and piercing the hand holding the access site as best illustrated in phantom in FIG. 4. The second and more important function of member 16 is to apply an amount of compressive force to the portion of sleeve 14 which it surrounds sufficient to enhance the inherent resiliency characteristics of that sleeve in the portion thereof which is not covered by member 16 to cause sleeve 14 to prevent air leaks into tube 12 during the time that needle 18 is in penetrated position extending through the upper wall portions of sleeve 14 and tube 12 as may be seen in FIG. 5. Another somewhat less important function of member 16 is to continuously apply such an amount of force to and through the body of member 16 to cause substantially immediate blockage of fluid leaks outward through the opening in tube 12 as needle 18 is drawn through the interface between the outer surface of the wall of tube 12 and the inner surface of sleeve 14, as is illustrated in FIG. 6. Momentarily later, as needle 18 is withdrawn through the body, or upper wall, portion of sleeve 14, the force applied to sleeve 14 by member 16 functions to cause leak-tight closure of the opening earlier generated by the penetration of needle 18, as shown by lines 20, 22 in FIG. 6. This latter force is applied majorly by the portions 16A, 16B of member 16, that is, the upper arm extremities which lie above the horizontal plane tangent to the upper surface of tube 12 as shown by dotted line 17 in FIG. 7.

The force applied by member 16 to sleeve 14 results from the strength of the material comprising member 16 to resist deformation from an original circular cross-section to the distorted cross-section it possesses when positioned around the portion of the periphery of sleeve 14 which it covers as shown in FIGS. 3 and 7. FIG. 7 is an expanded end view of the preferred access site 10 which is drawn to scale and shows the degree to which member 16 is distorted from its original circular cross-section when the material of tube 12 is plasticized polyvinyl chloride, elastomeric sleeve 14 is natural rubber latex and member 16 is polypropylene. Before assembly, tube 12 had an outside diameter of 0.253"±0.003"; latex sleeve 14 had an inner diameter of 0.219"±0.016", a wall thickness of 0.125"±0.010" and a nominal outside dieamter of 0.469". Sleeve 14 is mounted over tube 12 and its inner diameter is slightly stretched as it moves into position over the section of tube 12 preselected as the location for access site 10 and sleeve 14 concurrently applies a small compressive force on the outer diameter of tube 12. Similarly, prior to assembly, member 16 was an injection molded polypropylene member, circular in cross-section, having an inner diameter of 0.400" and a wall thickness of 0.052"-0.060" and an opening between the upper wall portions 16A and 16B of 0.125" as shown in FIGS. 3 and 7. Member 16 is mounted on sleeve 14 by forcing the portions 16A and 16B apart sufficiently to enable encirclement of the outside diameter of sleeve 14; the resistance of the polypropylene material to the spreading deformation sufficient to tightly overlie the illustrated portion of the periphery of sleeve 14 results in a bulging of the portion indicated by arrow 23 of sleeve 14 which lies between the inner surfaces 24A and 24B. Due to the final position spreading of arm portions 16A and 16B during assembly the portion indicated by arrow 25 of the wall of member 16 is slightly flattened from its circular cross-section producing a slightly elongated C-section which may be seen by rotating FIG. 7 until portion 16B is at the top of the figure.

As a result of the distortion of member 16 from its initial circular cross-section a combination of multi-directional forces are constantly applied to sleeve 14 by member 16. These forces are illustrated by the arrows 26 in FIG. 8 and are related to a needle 18 which is piercing sleeve 14 perpendicularly to the longitudinal axis of tube 12. It may be seen that the forces applied, primarily by the upper wall portions 16A and 16B, comprise forces consisting of components directed radially inwardly toward sleeve 12 and other forces which result from the squeezing pressure of surfaces 24A, and 24B on the outer surface of sleeve 14 to cause the bulging at 23 which have components which vary from the radial direction gradually upwardly to the horizontal and beyond toward the axially central area of the bulge 23.

FIG. 9 specifically illustrates the distribution of forces which are additionally available to cause closure, and leak-tight sealing, of a needle inserted through sleeve 14 at an angle less than 90°, and about 40° as shown, from a horizontal plane passing through the axis of tube 12, as indicated at 28, FIG. 6. Arrows 30 show the vertically oriented forces which bear on the upper and lower surface portions of the opening caused by needle 18 due to the angular insertion of the needle. The best sealing results are obtained with the access site construction of this invention when the needle penetration is made at an angle of approximately 45°±10° from a horizontal plane passing through the axis of tube 12. The access site shown in FIG. 7 and constructed from the materials above identified represents the best form of the invention that is currently known. It is satisfactory, however, to fabricate member 16 from materials other than polypropylene. The important requirements which must be satisfied is that the substitute material possess a relatively high rigidity and resistance to deformation from an initial circular cross-section to a C-shaped cross-section similar to that above described for polypropylene member 16. It is desirable to select a substitute having sufficient resistance to deformation in a relatively thin wall section, for example, less than 0.100 inch., to exert sufficient force to insure against leaks under severe use conditions. Satisfactory substitutes for polypropylene include other plastics such as synthetic polyamides available under the designation "Nylon", acetal resins available under the designation "Delrin", and ABS resins available from many suppliers.

The improvement in preventing air leaks using the preferred embodiment of this invention which has been specifically described above as to materials, initial and assembled sizes in the description of FIG. 7 is illustrated by the comparative test data set forth below. The preferred access site of this invention was tested in comparison with the access site construction of U.S. Pat. No. 3,814,137 which is commercially available from Travenol Laboratories, Inc. under the designation Travenol Dialysis Blood Set. Each of these constructions is especially suitable for use in blood sets employed in artificial kidney dialysis, and thus the test conditions selected for the comparison are conditions which are much more severe than the conditions encountered in normal clinical use on actual dialysis patients. The test conditions used are shown in Table I to provide a comparison with normal conditions encountered in clinical usage during dialysis employing a hollow fiber C-DAK artificial kidney.

TABLE I

|  | Selected Test Condition | Clinical Dialysis-Normal Range |
| --- | --- | --- |
| Needle | 18 gauge (0.05" diameter) | 20-27 gauge (0.036-0.016" diameter) |
| Angle of piercing | 90° | 45° |
| Pressure, sub-atmospheric | −150 to −400 mm Hg | 0 to −80 mm Hg |
| Pressure, positive | 5,10,15 psig | 0.4-3.0 psig |
| Fluid Flow Rate | 200 ml/minute | 100-300 ml/minute |
| Temperature | 37° C. ± 1° C. | 35°-39° C. |
| Fluid | Water | Blood |

It will be apparent that the conditions of larger needle size, angle of piercing, pressures both negative and positive and the use of water rather than blood are each substantially more severe than use conditions normally encountered.

The test procedure used was as follows:
1. Connect blood lines to negative pressure system and warm to body temperature, 37° C.
2. At water flow rate of 200 ml/min. set pressure to −150 mm Hg, which is approximately twice the maximum negative pressure usually encountered in dialysis.
3. Using 18 gauge, 0.050" diameter, needle pierce through the latex sleeve and the tube at a 90° angle to a horizontal plane passing through the axis of the blood tubes and hold in place for 1 minute, withdraw and inspect for leaks under bright light. If no leak, after 1 minute, then repeat and reinspect.
4. If no leak is visible after second inspection, raise subatmospheric pressure on water to −400 mm Hg. Repeat Step 3 for 2 piercings with 1 minute held before inspection.
5. If no leak after the four piercings of Steps 3 and 4, set pressure on water to positive 5 psig and repe. Step 3.
6. If no leak after the sixth piercing in Sten 5. change pressure to positive 10 psig and repeat Step 3.

7. If no leak after the eighth piercing of Step 6, change pressure to positive 15 psig and repeat Step 3. At any time a leak appeared in the form of a visible bubble or bubbles in the water in the Steps 3 or 4 or a leak around the needle or at the needle opening after withdrawal and after 1 minute of inspection time, the test was stopped and the number of piercings made before the leak occurred was recorded and the test discontinued.

Twenty access site constructions of the type shown in FIG. 2 of U.S. Pat. No. 3,814,137, available in the United States under the designation Travenol Dialysis Blood Set were obtained and tested under the selected test conditions by using the above stated test procedure in comparison to the preferred access site constructions of this invention, specifically shown in FIG. 7 and described above as to dimensions. The results are reported as the average number of needle punctures before a leak occurred, following for each access site the sequence of puncturing under the increasingly severe test conditions until failure occurred. The average number of punctures before a leak occurred for the access site constructions of U.S. Pat. No. 3,814,137 for the 20 sites tested was 5.25. The average number of punctures before a leak occurred for the preferred access site constructions of this invention for the 72 sites tested was 7.66.

To illustrate the necessity for sufficient forces to be generated by the needle-impenetrable sleeve within the body of the latex sleeve to prevent leaks, and for contrast with the results obtained from the use of the preferred embodiment of this invention as above shown, a further series of tests was conducted. In this series, each of the tube, the latex sleeve and the needle-impenetrable member was made of the same material as was used in the test of the preferred embodiment. The only change was the size of the latex sleeve, and it was decreased to an outside diameter of 0.438" and its inner diameter was 0.187". This change decreased the difference in diameter between the latex sleeve outside diameter and the impenetrable member inside diameter and concurrently increased the difference in outside diameter of the tube and the inside diameter of the latex sleeve. Seventy-two access sites of this construction, tested under identical conditions and by the same procedure resulted in an average number of punctures to leak of 2.53.

A total of twenty four hundred ninety six (2,496), each set having an arterial blood line and a venous blood line, blood sets were used in clinics during hemodialysis treatments of patients undergoing hemodialysis using hollow fiber artificial kidneys for treatment periods varying between about four to about six hours; each blood set was equipped with an access site of the preferred type shown in FIG. 7. Each access site was fabricated from polyvinyl chloride blood tubing, natural rubber latex sleeve and a polypropylene slotted tubular needle-impenetrable member having the nominal dimensions above specified.

Forty eight of these blood sets were used on patients suffering from acute renal failure and the arterial blood lines were punctured a total of 79 times using a twenty gauge needle without leaks; the venous blood lines were punctured a total of 67 times and three venous lines were punctured for continuous infusion of medicants throughout the treatments and two small leaks occurred when the twenty gauge needle was withdrawn from the latex sleeve but these leaks stopped quickly without requiring use of nylon locking ties of the type normally used prior to this invention. Of the other blood sets which were used on patients being treated for chronic renal failure, three minor leaks were detected on withdrawal of the twenty-two gauge needles being used and all three leaks sealed themselves with direct hand pressure applied over the injection site and without requiring the use of nylon ties to seal the leaks. It is apparent that this clinical use data demonstrates that the blood access site of this invention is safe and effective when used in typical acute and chronic dialysis treatment.

What I claim is:

1. An infusion tube access site comprising an infusion tube, an elongated elastomeric sleeve surrounding a portion of said infusion tube and a needle impenetrable plastic tubular member partially surrounding said sleeve for substantially the full length thereof, said tubular member being slotted axially from end to end and said slot being between and defined by inner end portions of the walls of said tubular member which extend above a horizontal plane passing through the diameter thereof, said tubular member having an inner diameter smaller than the outer diameter of said sleeve prior to assembly of said sleeve within said tubular member and said tubular member having a preselected wall thickness and resistance to deformation from a circular cross-section to provide compressive and radial pressure on said partially surrounded sleeve sufficient to cause said elastomeric sleeve to (bulge upwardly) deform from (a) its circular cross-section prior to assembly to a non-circular cross-section including an axially extending bulged portion lying within said slot, and said pressure on said sleeve and the resultant forces within said bulged portion being sufficient to prevent leaks into said tube during the time a needle pierces said sleeve and said tube, and to seal the opening resulting from withdrawal of said needle from said tube and said sleeve.

2. An infusion tube access site as set forth in claim 1 wherein said infusion tube is nontoxic and said tubular member is polypropylene.

3. An infusion tube access site as set forth in claim 1 wherein said nontoxic infusion tube is fabricated from a polyvinyl chloride polymer, and said tubular member is polypropylene.

4. An infusion tube access site as set forth in claim 1 wherein said tube is fabricated from a polyvinyl chloride polymer, said elastomeric sleeve is natural rubber latex and said tubular member is polypropylene.

* * * * *

UNITED STATES PATENT AND TRADEMARK OFFICE
CERTIFICATE OF CORRECTION

PATENT NO. : 4,184,489
DATED : January 22, 1980
INVENTOR(S) : Samuel Burd

It is certified that error appears in the above—identified patent and that said Letters Patent is hereby corrected as shown below:

Column 8, line 38, "(bulge upwardly)" and "(a)" should be deleted.

Signed and Sealed this

Twenty-seventh Day of October 1981

[SEAL]

Attest:

Attesting Officer

GERALD J. MOSSINGHOFF

Commissioner of Patents and Trademarks